(12) United States Patent
Roney, Jr. et al.

(10) Patent No.: US 6,399,949 B1
(45) Date of Patent: Jun. 4, 2002

(54) SYSTEM AND METHOD FOR DETECTING DEBONDING IN RUBBER COATED ROLLS

(75) Inventors: Robert Martin Roney, Jr., Schoharie; John William Devitt, Clifton Park; David Roy Parker, Worcester; Vladimir Pilic, Smithtown, all of NY (US)

(73) Assignee: General Electric Company, Schenectady, NY (US)

( * ) Notice: Subject to any disclaimer, the term of this patent is extended or adjusted under 35 U.S.C. 154(b) by 31 days.

(21) Appl. No.: 09/742,285

(22) Filed: Dec. 22, 2000

(51) Int. Cl.⁷ .......................... G01N 21/71; G01N 21/89
(52) U.S. Cl. ..................................... 250/341.6; 427/361
(58) Field of Search ...................... 250/341.6; 427/361, 427/374.1, 365; 428/481

(56) References Cited

U.S. PATENT DOCUMENTS 6,183,814 B1 * 2/2001 Nangeroni et al. ......... 427/361

\* cited by examiner

Primary Examiner—Constantine Hannaher
Assistant Examiner—Otilia Gabor
(74) Attorney, Agent, or Firm—Nixon & Vanderhye P.C.

(57) ABSTRACT

An infrared inspection system and an induction heating system used in conjunction enable the inspection of rubber coated rolls, such as rolls used in the pulp and paper industry. The system effects non-destructive inspections of rubber coated rolls to detect a debonded condition between the metal core and rubber coating. The method includes supporting a roll for inspection, evenly heating or cooling the roll, and observing a thermal transient of the roll generated by the evenly heating process. Using an infrared camera, observed areas that are not transferring heat uniformly with respect to neighboring areas are suspected debonded areas.

11 Claims, 3 Drawing Sheets

SYSTEM AND METHOD FOR DETECTING DEBONDING IN RUBBER COATED ROLLS

BACKGROUND OF THE INVENTION

The present invention relates to a system and method for rubber coated roll inspection and, more particularly, to an infrared inspection system cooperating with an induction heating system for non-destructive inspections of rubber coated rolls looking for de bonds between the metal core and rubber coating.

Industrial sites such as paper mills utilize large cylindrical rolls to process various products, such as paper pulp into sheets. The rolls are typically rubber coated and form one part of a large and expensive apparatus that is usually run continuously to maximize factory output. De bonding between the rubber coating and the base of the roll can occur over time, resulting in catastrophic consequences for the paper machine, particularly if the rubber coating is fully detached and pulled through the rest of the machine. The damage to the machine, the cost of re-coating the roll, and the factory downtime are of course cause for significant concern.

Some previous methods for rubber coating bond evaluation utilize acoustic emission, ultrasonic probes, and physical probing. Acoustic emission in a factory environment, however, is a difficult prospect as background noises and vibrations are difficult to effectively screen out, and reliable results have not been obtained. Ultrasonic probes have been used with mixed success, but high false alarm rates and subjectivity of results due to the hand held probing has limited the acceptance of this method. Moreover, roll inspection time is high. Physical probing with solid implements is also subjective and typically does not provide satisfactory results. The method includes "banging" the roll followed by listening to and feeling the, response, or attempting to induce minor displacements in the rubber coating and watching for variations.

BRIEF SUMMARY OF THE INVENTION

In an exemplary embodiment of the invention, a method of detecting debonding in coated paper rolls includes the steps of (a) supporting a roll for inspection, (b) evenly heating or cooling the roll, and (c) observing a thermal transient of the roll generated according to step (b). Step (b) may be practiced by securing an induction coil around the roll, activating the induction coil, and axially displacing the induction coil along a length of the roll. The induction coil is preferably supported by a robotic vehicle, wherein the axial displacing of the induction coil is practiced by controlling the position of the robotic vehicle. Step (c) is preferably practiced by capturing infrared images of the heated roll and determining de bonded areas according to the infrared images, which may be displayed on a display or the like.

In another exemplary embodiment of the invention, an inspection system for detecting debonding in coated paper rolls includes a heating or cooling unit attachable to a roll for evenly heating or cooling a roll, and a receptor observing a thermal transient of a roll generated by the heating or cooling unit.

DETAILED DESCRIPTION OF THE INVENTION

Figure 1:
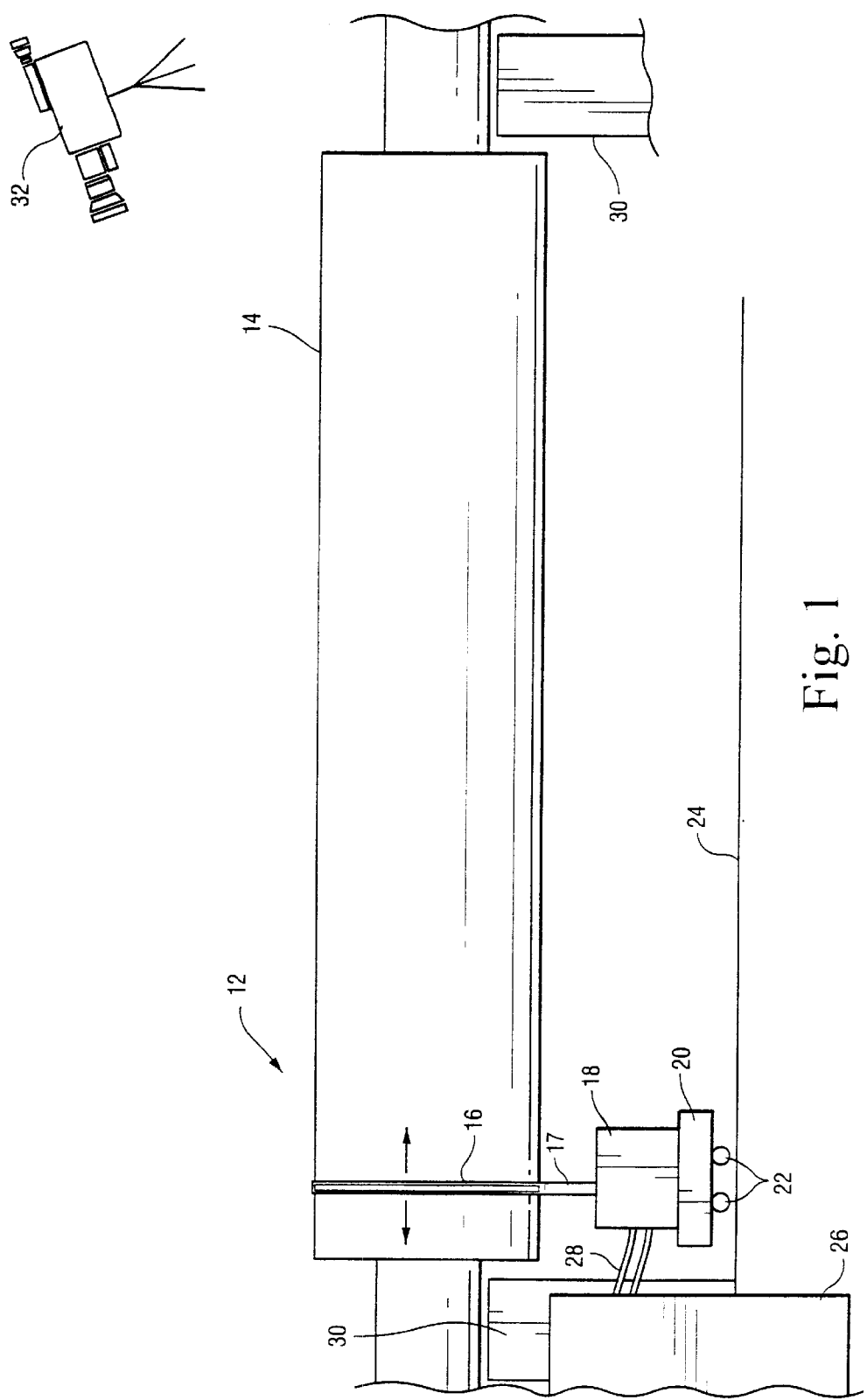
FIG. 1 is a schematic illustration of the inspection system according to the present invention.

It has been discovered that a de bonded condition between a metal core and rubber coating in a cylindrical industrial roll, such as a roll used in a paper manufacturing process, does not transfer heat evenly or uniformly with respect to a bonded area. Thus, with the present invention, an induction system generates a thermal transient, and the inspection area is viewed with an infrared camera to detect the de bonded condition. With reference to FIG. 1, the inspection system includes an induction heating system 12 that serves to heat the metal underneath the rubber coating of a cylindrical roll 14. As noted, an example of a covered roll suitable for the inspection system of the invention is a rubber coated paper roll used in the paper manufacturing process. The invention, however, is not meant to be limited to this specific example.

Figure 3:
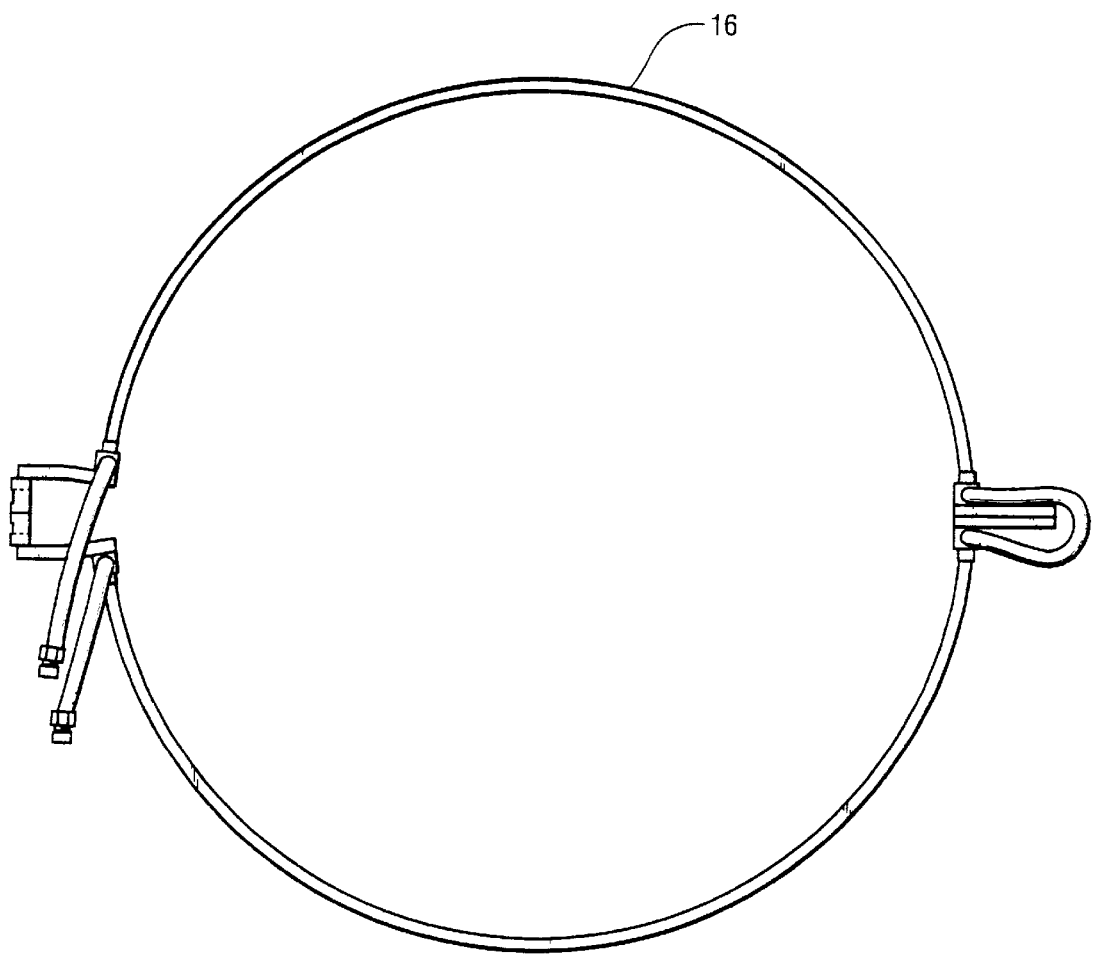
FIG. 3 shows induction coils that form part of the induction heating system.

The induction heating system 12 includes a plurality of induction coils 16 configured to surround an outer diameter of the roll 14. The coils 16 are hinged at at least one point as shown in FIG. 3 (two points shown) to eliminate roll manipulation for coil mounting. The space between the induction coils 16 and the roll 14 is dependent on the size of the roll. A bus bar extender 17 or the like serves to ensure that the coils 16 are properly positioned. The coils 16 are coupled with a heat station 18, which in turn is supported by a robotic tractor 20 or the like. The robotic tractor 20 includes wheels 22 set on a track 24. The tractor 20 and induction heating system 12 are known, although not necessarily for use in conjunction with each other per se, and any suitable construction can be used. An example of a suitable tractor is the BUG-O modular drive system available from Bug-0 Systems, Inc. of Pittsburgh, Pennsylvania. An example of a suitable induction heating system is available from Inner Power of Almont, Mich.

The heat station 18 and tractor 20 are coupled to a power source 26 by suitable cables 28 or the like. The temperature of the induction coils 16 via the heat station 18 is set based on numerous factors, including the size of the roll, the material of the roll, etc., to most efficiently heat the roll.

In order to perform a debonding detection, the roll 14 is first supported in a lathe or set of stands or the like 30 (shown schematically in FIG. 1). Preferably, a supporting lathe 30 is used that enables the roll 14 to be rotated during heating to reduce non-uniformities. The induction heating system 12 is activated and the tractor 20 is driven along a length of the roll 14 while the roll 14 is rotated by the supporting lathe 30 to evenly heat the roll 14. The induction heating system 12 may be passed over the length of the roll a single time or numerous times, for example 3–9 times, to produce a thermal transient for performing the inspection of the rubber to metal bond region and to more evenly heat the inspection area. With the induction heating system 12, the metal core of the roll 14 is heated first, and the heat is absorbed by the rubber coating. By slowly heating the core using multiple passes, the rubber and metal can expand gradually, resulting in more accurate results. Moreover, the low heating rate insures maximum contrast between the bonded regions and the de bonded regions. Prior to the inspection for de bonded areas, the entire roll is inspected for uniform heating with a pre-inspection temperature sweep by the infrared camera, using a small temperature span so as to detect small anomalies in a widely varying temperature zone.

Figure 2:
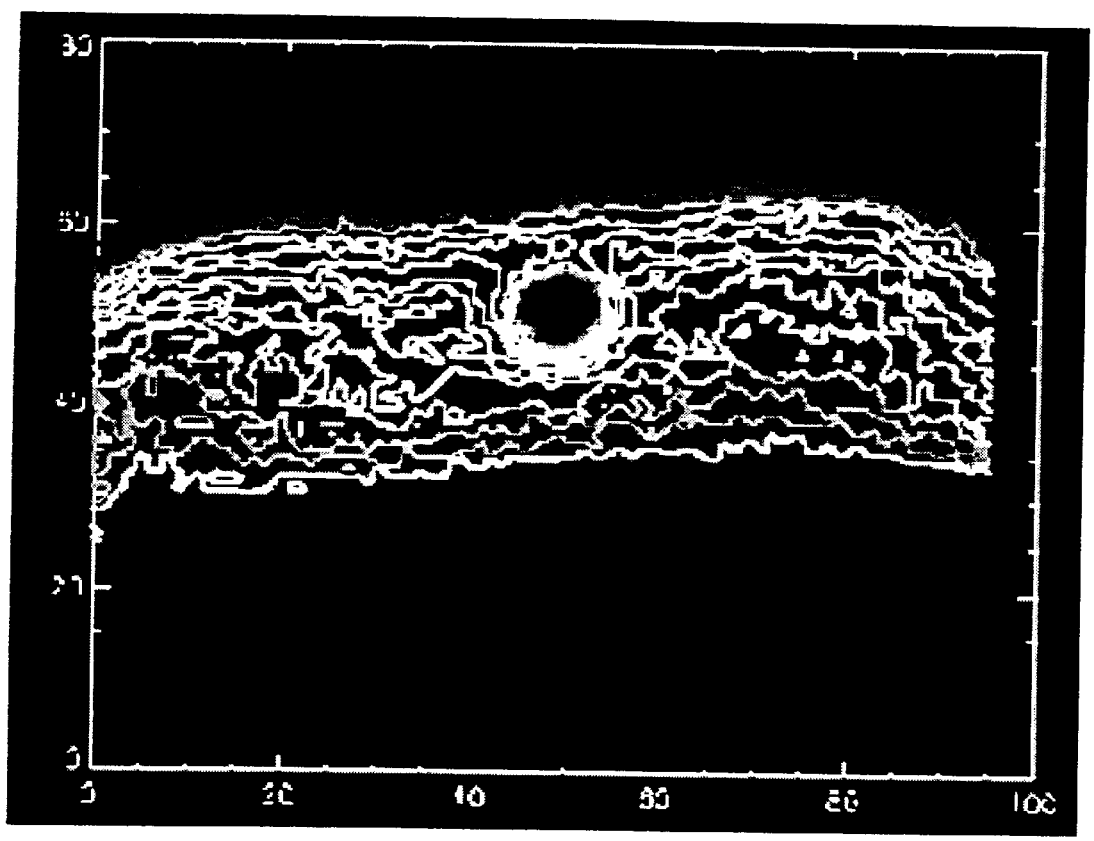
FIG. 2 is an exemplary infrared image used for detecting debonding.

As the heat is absorbed by the rubber coating, the inspection area is viewed with an infrared camera 32, which sends an infrared image, such as that shown in FIG. 2, to a display or other output for further analysis. A viewing position of the infrared camera 32 is changed manually in sections to follow the inspection area as the induction coils 16 are moved axially along the length of the roll 14.

As seen in FIG. 2, the infrared camera 32 can detect heating anomalies in the rubber coating, which correspond to a bonding condition between the rubber coating and metal core of the roller 14. Inspection zone size is preferably between 12"–48"in length to provide a reasonable area for comparison. If this inspection zone size is too small, the size of the, normally bonded area for comparison with de bonds would be insufficient; whereas if the inspection zone size is too large, the temperature non-uniformities would become too large.

The infrared camera 32 itself is also known. In order to facilitate result analysis, the camera 32 is set for reverse contrast to better display cool debond conditions. That is, with the reverse contrast camera setting, cooler areas in the inspection zone are brighter on the infrared image.

With continued reference to FIG. 2, using known methods incorporating spatial derivative and fourier analysis, an analysis may be conducted to determine the sharpness of features on the roll surface to indicate a depth of the debonding condition. In this context, such an analysis can provide an indication of flaws in the thickness of the rubber coating and the like.

In another operating mode of the invention, a debonding condition can be detected in situ. In this regard, in operation, the roll 14 is heated by the normal manufacturing process. The known induction system incorporates a chiller unit that effects water cooling of the hot roll. This cooling produces a contrast of debonded areas that can be detected using the infrared camera 32. A computer card captures the raw images from the IR camera. The inspector equipped with a wearable PC transfers the images on-line to be annotated and stored to the PC for post processing and reporting. Standard software steps are used to enhance contrast of the image. These steps include using spatial derivatives, resealing, FFT's and color enhancements. These software steps can result in an image with highlighted flaw areas. The end result is a report that is completed near real time.

With the structure and method of the invention, debonds between a metal core and rubber coating of a rubber coated roll can be detected via a non-destructive inspection. By evenly heating or cooling the metal core and rubber coating of the roll with an induction heating system or chiller system, a thermal transient can be generated, which can be detected by an infrared camera. Areas that are not transferring heat evenly as detected by the infrared camera are suspected debonded areas.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method of detecting debonding in coated paper rolls, the method comprising:

(a) supporting a roll for inspection;
    (b) evenly heating or cooling the roll; and
    (c) observing a thermal transient of the roll generated according to step (b).

2. A method according to claim 1, wherein step (b) is practiced by securing an induction coil around the roll, activating the induction coil, and axially displacing the induction coil along a length of the roll.

3. A method according to claim 2, wherein the induction coil is supported by a robotic vehicle, and wherein the step of axially displacing the induction coil is practiced by controlling a position of the robotic vehicle.

4. A method according to claim 2, wherein step (b) is further practiced by repeatedly axially displacing the induction coil back and forth along the length of the roll.

5. A method according to claim 1, wherein step (c) is practiced by capturing infrared images of the roll and determining debonded areas according to the infrared images.

6. A method according to claim 5, wherein step (c) is further practiced by displaying the infrared images.

7. A method according to claim 1, wherein step (a) is practiced by rotating the roll during step (b).

8. An inspection system for detecting debonding in coated paper rolls, the inspection system comprising:

a heating or cooling unit attachable to a roll for evenly heating or cooling the roll; and
    a receptor observing a thermal transient of the roll generated by the heating or cooling unit.

9. An inspection system according to claim 8, wherein the heating unit comprises an induction coil.

10. An inspection system according to claim 8, further comprising a robotic vehicle supporting the induction coil, the robotic vehicle controlling a position of the induction coil along a length of the roll.

11. An inspection system according to claim 8, wherein the receptor comprises an infrared camera.

* * * * *

UNITED STATES PATENT AND TRADEMARK OFFICE
CERTIFICATE OF CORRECTION

PATENT NO.    : 6,399,949 B1
DATED         : June 4, 2002
INVENTOR(S)   : Roney, Jr. et al.

It is certified that error appears in the above-identified patent and that said Letters Patent is hereby corrected as shown below:

Column 1,
Line 9, delete "de bonds" and insert -- debonds --;
Line 16, delete "De bonding" and insert -- Debonding --;
Line 36, delete "the," and insert -- the --;
Line 53, delete "de bonded" and insert -- debonded --.

Column 2,
Line 6, delete "de bonded" and insert -- debonded --;
Line 12, delete "de bonded" and insert -- debonded --;
Line 62, delete "de bonded" and insert -- debonded --;
Line 62, delete "de bonded" and insert -- debonded --.

Column 3,
Line 14, delete "the," and insert -- the --;
Line 14, delete "de bonds" and insert -- debonds --.

Signed and Sealed this

Twenty-third Day of July, 2002

Attest:

Attesting Officer

JAMES E. ROGAN
*Director of the United States Patent and Trademark Office*